United States Patent [19]

Zeng et al.

[11] Patent Number: 6,084,080

[45] Date of Patent: Jul. 4, 2000

[54] BREVISCAPINUM AND EXTRACTING PROCESS THEREOF FROM ERIGERON BREVISCAPUS

[75] Inventors: Lipin Zeng; De Pu, both of City of Industry, Calif.

[73] Assignee: Farlong International Inc., City of Industry, Calif.

[21] Appl. No.: 09/232,082

[22] Filed: Jan. 15, 1999

[51] Int. Cl.⁷ ............................. A01N 65/00; C07H 15/00
[52] U.S. Cl. ............................................. 536/8; 424/195.1
[58] Field of Search ................................ 424/195.1; 536/8

[56] References Cited

U.S. PATENT DOCUMENTS 5,443,839  8/1995  Meybeck ................................. 424/450

OTHER PUBLICATIONS

Computer Derwent Abstract Guo et al CN–104038 "Erigeron Breviscapus Basic Element Freeze Drying Preparation" Apr. 10, 1995.

*Primary Examiner*—Herbert J. Lilling
*Attorney, Agent, or Firm*—Raymond Y. Chan; David and Raymond

[57] ABSTRACT

An extracting process for extracting breviscapinum from erigeron breviscapus, wherein the breviscapinum has a chemical structure of 4',5,6-trishydroxyflavone-7-glucuronide that can increases cerebral blood flow for significantly decreasing cerebrovascular resistance; raises permeability of blood-brain barrier, increases nutritional blood flow of myocardium; raises immune function of body macrophage cell and counteraction against blood and oxygen depletion induced by hypophyseal pitutrin and thrombocyte agglutination induced by adenosine diphespate inhibiting internal thrombosis and promoting activity of cellulose dissolution; and increases peripheral and coronary bleed flow, effective for sequelas induced by cerebrovascular accident: palsy, coronary heart disease and angina pectoris.

25 Claims, No Drawings

BREVISCAPINUM AND EXTRACTING PROCESS THEREOF FROM ERIGERON BREVISCAPUS

FIELD OF THE PRESENT INVENTION

The present invention relates to erigeron breviscapus, and more particularly to an extracting process for producing breviscapinum from the erigeron breviscapus.

BACKGROUND OF THE PRESENT INVENTION

According to Chinese (herbal) medicine such as Compendium of Materia Medica, erigeron breviscapus is a kind of plant that can increase cerebral blood flow, decrease cerebrovascular resistance, improve immune function of body macrophage cell, and etc. However, in fact, the whole plant of erigeron breviscapus contains numerous of chemicals that only one essential element within the erigeron breviscapus provides the above medical functions. Therefore, if we can successfully find out and extract that functional chemical from the erigeron breviscapus, the patients can effectively take dose of concentrated functional chemical as the herbal medicine instead of having the whole plant of erigeron breviscapus, including all other non-functional elements within the plant. Like the Western medicine, it is more efficient and effective.

SUMMARY OF THE PRESENT INVENTION

The main object of the present invention is to provide a process of extracting a breviscapinum from erigeron breviscapus, wherein the breviscapinun has a chemical structure of "4',5,6-trishydroxyflavone-7-glucuronide" which is proved to be the functional element within the erigeron breviscapus, that:

(1) increases cerebral blood flow for significantly decreasing cerebrovascular resistance;

(2) raises permeability of blood-brain barrier, increases nutritional blood flow of myocardium;

(3) raises immune function of body macrophage cell and counteraction against blood and oxygen depletion induced by hypophyseal pitutrin and thrombocyte agglutination induced by adenosine diphespate inhibiting internal thrombosis and promoting activity of cellulose dissolution;

(4) increases peripheral and coronary bleed flow, effective for sequelas induced by cerebrovascular accident: palsy, coronary heart disease and angina pectoris.

DETAILED DESCRIPTION OF THE PREFERRED EMBODIMENT

According to the present invention, breviscapinum is proved to be the functional element within the erigeron breviscapus, that increases cerebral blood flow for significantly decreasing cerebrovascular resistance; raises permeability of blood-brain barrier; increases nutritional blood flow of myocardium; raises immune function of body macrophage cell and counteraction against blood and oxygen depletion induced by hypophyseal pitutrin and thrombocyte agglutination induced by adenosine diphespate inhibiting internal thrombosis and promoting activity of cellulose dissolution; and increases peripheral and coronary bleed flow, effective for sequelas induced by cerebrovascular accident: palsy, coronary heart disease and angina pectoris.

Wherein, the breviscapinum has the following chemical structure:

4',5,6-trishydroxyflavone-7-glucuronide

Moreover, the breviscapinum has a chemical formula as follow:

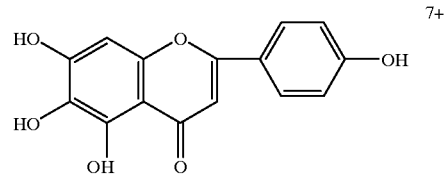

The breviscapinum can be extracted from the erigeron breviscapus by an extracting process including the following steps:

(1) Grind whole plants of erigeron breviscapus, for example 5 kg according to the present preferred embodiment, to form the erigeron breviscapus coarse powder.

(2) Soak an erigeron breviscapus coarse powder, which is made from erigeron breviscapus, with industry ethanol to form a soaking solution. This step (1) further comprises the sub-steps of (a) soaking the erigeron breviscapus coarse powder with industry ethanol of 80% purity in a ratio of 1:1.5–2 for three days;

(b) filtering out a first soaking solution and forming a first erigeron breviscapus precipitate;

(c) soaking the first erigeron breviscapus precipitate again with industry ethanol of 80% purity in a ratio of 1:1.5–2 for three days again and then filtering out a second soaking solution and forming a second erigeron breviscapus precipitate;

(d) soaking the second erigeron breviscapus precipitate one more time with industry ethanol of 80% purity in a ratio of 1:1.5–2 for three days and then filtering out a third soaking solution; and (e) mixing the first, second and third soaking solutions to form a combined soaking solution.

(3) Concentrate the combined soaking solution by using a vacuum distillation at 60° C. to thicker and thicker form until a cream color volatile oil is evaporated and distilled out of the combined soaking solution to form a concentrate.

(4) Dissolve the concentrate in boiling water (2500 ml according to the present embodiment) in a ratio of 1:1.5–2 to obtain a water dissolvable filtered solution, wherein it comprises the sub-steps of:

(a) adding and stirring the boiling water with the concentrate until the concentrate is dissolved in the boiling water; and (b) filtering the dissolved concentrate when it is still hot to form the filtered solution and a water indissoluble precipitate; and (c) degreasing the filtered solution under 30° C.–60° C. for three times by using petroleum ether.

(5) Extract the degreased filtered solution with chloroform in a ratio of 1:1 for three times to separate out the juniper acid to form a first extracted and a chloroform liquid. According to the present embodiment, 500 ml of chloroform is used for each extraction.

(6) Extract the first extracted solution with ethyl ether in a ratio of 1:1 for five times to separate out the flavonoid fraction thereof to form a second extracted solution and an ethyl ether liquid. According to the present embodiment, 500 ml of ethyl ether is used for each extraction.

(7) Extract the second extracted solution with ethyl acetate in a ratio of 1:1 for six times to separate out the flavone and acetate content to form a third extracted solution and an ethyl acetate liquid. According to the present embodiment, 500 ml of ethyl acetate is used for each extraction.

(8) Extract the third extracted solution with saturated water of solution of lead acetate in a ratio of 1:1 to form a fourth extracted solution and an extracted precipitate in yellow color.

(9) Filter out the extracted precipitate.

(10) Suspend the yellow extracted precipitate in ethanol of 95% purity in a ratio of 1:1–1.5 and add diluted sulphuric acid to filter and separate out the lead content to obtain an ethanol solution and a lead sulphuric acid.

(11) Filter, depressurize and concentrate the ethanol solution under vacuum condition to an adequate volume until yellow precipitate is obtained, wherein the yellow precipitate is in tiny needle crystalline when observing under the microscope.

(12) Further wash and filter the yellow precipitate with ethanol to obtain a final precipitate.

(13) Dry the final precipitate under infrared lighting to achieve coarse breviscapinum. According to the present embodiment, 10.2 g of coarse breviscapinum can be achieved from the 5 kg of erigeron breviscapus.

(14) Re-crystallize the coarse breviscapinum with methanol to obtain the crystallized pure breviscapinum having a purity of more than 95% and a chemical structure of 4',5,6-trishydroxyflavone-7-glucuronide that is determined by using elementary analysis, mass spectrographic analysis and nuclear magnetic resonance. According to the present embodiment, 6 g of crystallized pure breviscapinum can be obtained.

The breviscapinum (4',5,6-trishydroxyflavone-7-glucuronide) produced in the present invention has a melting point of 320° C. It is in orange color when reacting with the hydrochloric acid magnesium ribbon. The breviscapinum turns dark blue color with the ferric chloride test solution. The ultraviolet spectrograph of the breviscapinum of the present invention is λmax 286 mm, 337 mm.

What is claimed is:

1. An extracting process for producing a breviscapinum which has a chemical structure of 4',5,6-trishydroxyflavone-7-glucuronide, comprising the steps of:

(a) providing an erigeron breviscapus powder by grinding whole plant of erigeron breviscapus;

(b) soaking said erigeron breviscapus powder with industry ethanol to form a soaking solution;

(c) concentrating said soaking solution until a cream color volatile oil is distilled out of said soaking solution to form a concentrate;

(d) dissolving said concentrate in boiling water to obtain a water dissolvable filtered solution;

(e) degreasing said filtered solution to form a degreased filtered solution;

(f) extracting said degreased filtered solution with chloroform to form a first extracted and a chloroform liquid;

(g) extracting said first extracted solution with ethyl ether to form a second extracted solution and an ethyl ether liquid;

(h) extracting said second extracted solution with ethyl acetate to form a third extracted solution and an ethyl acetate liquid;

(i) extracting said third extracted solution with lead acetate to form a fourth extracted water dissolvable and an extracted precipitate in yellow color;

(j) filtering out said extracted precipitate;

(k) suspending said extracted precipitate in ethanol and add diluted sulphuric acid to filter and separate out lead content in order to obtain an ethanol solution and a lead sulphuric acid;

(l) filtering, depressurizing and concentrating said ethanol solution to an adequate volume until yellow precipitate is obtained, wherein said yellow precipitate is in tiny needle crystalline when observing under microscope;

(m) further washing and filtering said yellow precipitate with ethanol to obtain a final precipitate; and (n) drying said final precipitate to obtain a coarse breviscapinum.

2. The extracting process as recited in claim 1, after step (n), further comprising a step of recrystallizing said coarse breviscapinum with methanol to obtain said breviscapinum.

3. The extracting process as recited in claim 1 wherein the step (b) comprises the steps of soaking said erigeron breviscapus powder with a first dose of industry ethanol of 80% purity for three days; filtering out a first soaking solution and forming a first erigeron breviscapus precipitate; soaking said first erigeron breviscapus precipitate again with a second dose of industry ethanol of 80% purity for three days and then filtering out a second soaking solution and forming a second erigeron breviscapus precipitate; soaking said second erigeron breviscapus precipitate one more time with a third dose of industry ethanol of 80% purity for three days and then filtering out a third soaking solution; and mixing and combining said first, second and third soaking solutions to form said soaking solution.

4. The extracting process as recited in claim 2 wherein the step (b) comprises the steps of soaking said erigeron breviscapus powder with a first dose of industry ethanol of 80% purity for three days; filtering out a first soaking solution and forming a first erigeron breviscapus precipitate; soaking said first erigeron breviscapus precipitate again with a second dose of industry ethanol of 80% purity for three days and then filtering out a second soaking solution and forming a second erigeron breviscapus precipitate; soaking said second erigeron breviscapus precipitate one more time with a third dose of industry ethanol of 80% purity for three days and then filtering out a third soaking solution; and mixing and combining said first, second and third soaking solutions to form said soaking solution.

5. The extracting process as recited in claim 1 wherein, in step (c), said soaking solution is concentrated at 60° C.

6. The extracting process as recited in claim 4 wherein, in step (c), said soaking solution is concentrated at 60° C.

7. The extracting process as recited in claim 1 wherein the step (d) comprises the steps of adding and stirring equal amount of boiling water with said concentrate until said concentrate is dissolved in said boiling water; filtering said hot dissolved concentrate to form said filtered solution and a water indissoluble precipitate; and degreasing said filtered solution under 30° C.–60° C. for three times by petroleum ether.

8. The extracting process as recited in claim 6 wherein the step (d) comprises the steps of adding and stirring equal amount of boiling water with said concentrate until said concentrate is dissolved in said boiling water; filtering said hot dissolved concentrate to form said filtered solution and a water indissoluble precipitate; and degreasing said filtered solution under 30° C.–60° C. for three times by petroleum ether.

9. The extracting process as recited in claim 1 wherein, in step (f), said degreased filtered solution is extracted with chloroform for three times to separate out juniper acid.

10. The extracting process as recited in claim 8 wherein, in step (f), said degreased filtered solution is extracted with said chloroform for three times to separate out juniper acid thereof.

11. The extracting process as recited in claim 1 wherein, in step (g), said first extracted solution is extracted with said ether for five times to separate out flavonoid fraction thereof.

12. The extracting process as recited in claim 10 wherein, in step (g), said first extracted solution is extracted with said ether for five times to separate out flavonoid fraction thereof.

13. The extracting process as recited in claim 1 wherein, in step (h), said second extracted solution is extracted with ethyl acetate for six times to separate out flavone and acetate content thereof.

14. The extracting process as recited in claim 12 wherein, in step (h), said second extracted solution is extracted with ethyl acetate for six times to separate out flavone and acetate content thereof.

15. The extracting process as recited in claim 14 wherein, in step (k), said ethanol has a 95% purity.

16. The extracting process as recited in claim 15 wherein, in step (b) said erigeron breviscapus powder is soaked with said industry ethanol in a ration of 1:1.5 to 2; in step (d), said concentrate is dissolved in said boiling water in a ratio of 1:1.5 to 2; in step (f), said degreased filtered solution is extracted with said chloroform in a ratio of 1:1; in step (g), said first extracted solution is extracted with said ethyl ether in a ratio of 1:1; in step (h), said second extracted solution is extracted with said ethyl acetate in a ratio of 1:1; in step (i), said third extracted solution is extracted with said saturated water of solution of lead acetate in a ratio of 1:1; in step (k), said yellow extracted precipitate is suspended in said ethanol in a ratio of 1:1 to 1.5.

17. The extracting process as recited in claim 1 wherein, in step (n), said final precipitate is dried under infrared lighting.

18. The extracting process as recited in claim 15 wherein, in step (n), said final precipitate is dried under infrared lighting.

19. The extracting process as recited in claim 16 wherein, in step (n), said final precipitate is dried under infrared lighting.

20. The extracting process as recited in claim 15 wherein 10.2 g of coarse breviscapinum is obtained from 5 kg of erigeron breviscapus, wherein 2500 ml of said boiling water is used in step (d), 500 ml of said chloroform is used for each extraction in step (f), 500 ml of said ethyl ether is used for each extraction in step (g), and 50 ml of said ethyl acetate is used for each extraction in step (h).

21. The extracting process as recited in claim 19 wherein 10.2 g of coarse breviscapinum is obtained from 5 kg of erigeron breviscapus, wherein 2500 ml of said boiling water is used in step (d), 500 ml of said chloroform is used for each extraction in step (f), 500 ml of said ethyl ether is used for each extraction in step (g), and 50 ml of said ethyl acetate is used for each extraction in step (h).

22. The extracting process as recited in claim 19 wherein 10.2 g of coarse breviscapinum is obtained from 5 kg of erigeron breviscapus, wherein 2500 ml of said boiling water is used in step (d), 500 ml of said chloroform is used for each extraction in step (f), 500 ml of said ethyl ether is used for each extraction in step (g), and 50 ml of said ethyl acetate is used for each extraction in step (h).

23. The extracting process as recited in claim 20 wherein 6 g of said breviscapinum is obtained.

24. The extracting process as recited in claim 21 wherein 6 g of said breviscapinum is obtained.

25. The extracting process as recited in claim 22 wherein 6 g of said breviscapinum is obtained.

* * * * *